US010588487B2

United States Patent
Hagihara

(10) Patent No.: US 10,588,487 B2
(45) Date of Patent: Mar. 17, 2020

(54) SIGNAL TRANSMISSION CIRCUIT AND ENDOSCOPE SYSTEM

(71) Applicant: OLYMPUS CORPORATION, Hachioji-shi, Tokyo (JP)

(72) Inventor: Yoshio Hagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 107 days.

(21) Appl. No.: 15/886,262

(22) Filed: Feb. 1, 2018

(65) Prior Publication Data

US 2018/0153374 A1 Jun. 7, 2018

Related U.S. Application Data

(63) Continuation of application No. PCT/JP2015/077278, filed on Sep. 28, 2015.

(51) Int. Cl.
*A61B 1/00* (2006.01)
*H03F 1/56* (2006.01)
(Continued)

(52) U.S. Cl.
CPC ...... *A61B 1/00011* (2013.01); *A61B 1/00006* (2013.01); *A61B 1/00009* (2013.01); (Continued)

(58) Field of Classification Search
CPC . A61B 1/00011; A61B 1/045; A61B 1/00018; A61B 1/00009; A61B 1/00006;
(Continued)

(56) References Cited

U.S. PATENT DOCUMENTS

2008/0170846 A1* 7/2008 Wang .................. A61B 1/00096
396/182
2008/0284539 A1* 11/2008 Tateoka .................... H03F 1/56
333/124
(Continued)

FOREIGN PATENT DOCUMENTS

| JP | 2004-23135 A | 1/2004 |
|---|---|---|
| WO | 2014/171316 A1 | 10/2014 |
| WO | 2015/141333 A1 | 9/2015 |

OTHER PUBLICATIONS

International Search Report dated Dec. 22, 2015, issued in counterpart International Application No. PCT/JP2015/077278, w/English translation (2 pages).

*Primary Examiner* — Jared Walker
(74) *Attorney, Agent, or Firm* — Westerman, Hattori, Daniels & Adrian, LLP

(57) ABSTRACT

A signal transmission circuit includes an impedance conversion circuit and a current-voltage conversion circuit. A first current is input to the impedance conversion circuit. The impedance conversion circuit outputs a second current according to the first current. The current-voltage conversion circuit converts the second current output from the impedance conversion circuit into a voltage. The impedance conversion circuit includes a first current source and a current output circuit. The first current source generates a reference current. The current output circuit outputs the second current according to the difference between the first current and the reference current or the sum of the first current and the reference current.

4 Claims, 10 Drawing Sheets

(51) Int. Cl.
  *H03F 3/45*  (2006.01)
  *H03F 3/50*  (2006.01)
  *A61B 1/045*  (2006.01)
(52) U.S. Cl.
  CPC .......... *A61B 1/00018* (2013.01); *A61B 1/045* (2013.01); *H03F 1/56* (2013.01); *H03F 3/45475* (2013.01); *H03F 3/505* (2013.01); *A61B 1/00045* (2013.01)
(58) Field of Classification Search
  CPC . A61B 1/00045; H03F 3/505; H03F 3/45475; H03F 1/56
  USPC .......................................................... 348/65
  See application file for complete search history.

(56) References Cited

U.S. PATENT DOCUMENTS

| | | | | |
|---|---|---|---|---|
| 2016/0345810 | A1* | 12/2016 | Hiraide | A61B 1/041 |
| 2017/0150869 | A1* | 6/2017 | Adachi | A61B 1/04 |
| 2017/0179961 | A1* | 6/2017 | Itasaka | H03B 5/362 |

* cited by examiner

US 10,588,487 B2

SIGNAL TRANSMISSION CIRCUIT AND ENDOSCOPE SYSTEM

This is a continuation application based on International Patent Application No. PCT/JP2015/077278, filed Sep. 28, 2015, the content of which is incorporated herein by reference.

BACKGROUND OF THE INVENTION

Field of the Invention

The present invention relates to a signal transmission circuit and an endoscope system.

Description of Related Art

FIG. 9 shows a configuration of a signal transmission circuit 1100 according to a related art. The signal transmission circuit 1100 is a first example of the related art. The signal transmission circuit 1100 has an impedance conversion circuit 1120 and a current-voltage conversion circuit 1130. A drive circuit 1110 is disposed at the input side of the signal transmission circuit 1100.

The drive circuit 1110 has a transistor M10. The transistor M10 is an NMOS transistor. A drain terminal of the transistor M10 is connected to a power supply VDD. A source terminal of the transistor M10 is connected to a transmission cable CB11. An input signal VIN is input to a gate terminal of the transistor M10. The drive circuit 1110 converts the input signal VIN into a current according to transconductance gm of the transistor M10. The current value generated by the drive circuit 1110 is $I_{IN}$. The current generated by the drive circuit 1110 is input to the impedance conversion circuit 1120 via the transmission cable CB11 and a matching element Z11 for impedance matching.

The impedance conversion circuit 120 has a current output circuit 1150. The current output circuit 1150 has a transistor M11 and a transistor M12 which constitute a current mirror. The transistors M11 and M12 are NMOS transistors. A drain terminal of the transistor M11 is connected to an input terminal Tin. A source terminal of the transistor M11 is connected to ground GND. A gate terminal of the transistor M11 is connected to the drain terminal of the transistor M11. A drain terminal of the transistor M12 is connected to an output terminal Tout. A source terminal of the transistor M2 is connected to the ground GND. A gate terminal of the transistor M12 is connected to the gate terminal of the transistor M11.

The current generated by the drive circuit 1110 is input to the input terminal Tin. This current flows between the drain and source terminals of the transistor M11. A current according to a mirror ratio of the transistors M11 and M12 flows between the drain and source terminals of the transistor M12. It is now assumed that the W/L ratios of the transistors M11 and M12 are the same. When the coefficient of the transistor M11 is m and the coefficient of the transistor M12 is n, a current value of the current flowing through the transistor M12 is $(n/m) \times I_{IN}$. When the coefficients of the transistors M11 and M12 are the same, currents flowing through the transistors M11 and M12 are the same. The impedance conversion circuit 1120 outputs a current whose current value is $I_{OUT}$ through the output terminal Tout. The impedance conversion circuit 1120 is a current conversion circuit having low input impedance and high output impedance.

The current-voltage conversion circuit 1130 has a feedback resistor R12 and an operational amplifier OP11. A first terminal of the feedback resistor R12 is connected to an inverting input terminal of the operational amplifier OP11. A second terminal of the feedback resistor R12 is connected to an output terminal of the operational amplifier OP11. The inverting input terminal of the operational amplifier OP11 is connected to the impedance conversion circuit 1120. A non-inverting input terminal of the operational amplifier OP11 is connected to a power supply that outputs a reference voltage VREF.

The current output from the impedance conversion circuit 1120 is input to the current-voltage conversion circuit 1130. The current-voltage conversion circuit 1130 converts the current into a voltage and outputs the voltage as an output signal VOUT.

FIG. 10 shows a configuration of a signal transmission circuit 1101 according to a related art. The signal transmission circuit 1101 is a second example of the related art. The signal transmission circuit 1101 has an impedance conversion circuit 1121 and a current-voltage conversion circuit 1130. A drive circuit 1110 is disposed at the input side of the signal transmission circuit 1101.

The drive circuit 1110 and the current-voltage conversion circuit 1130 are identical to the drive circuit 1110 and the current-voltage conversion circuit 1130 in FIG. 9. Therefore, descriptions of the drive circuit 1110 and the current-voltage conversion circuit 1130 will be omitted.

The impedance conversion circuit 1121 has a transistor M13, a current source CS11, and a current source CS12. The transistor M13 is an NMOS transistor. The transistor M13 is a gate-grounded transistor. A source terminal of the transistor M13 is connected to an input terminal Tin. A drain terminal of the transistor M13 is connected to an output terminal Tout. A gate terminal of the transistor M13 is connected to a power supply V11.

A first terminal of the current source CS11 is connected to a power supply VDD. A second terminal of the current source CS11 is connected to the output terminal Tout. A first terminal of the current source CS12 is connected to the input terminal Tin. A second terminal of the current source CS12 is connected to ground GND. The current source CS11, the transistor M13, and the current source CS12 are connected in series between the power supply VDD and the ground GND.

A current generated by the drive circuit 1110 is input to the input terminal Tin. A constant current whose current value is $I_1$ flows through the current source CS12. A constant current whose current value is $I_2$ flows through the current source CS11. The impedance conversion circuit 1121 outputs a current whose current value is $I_{OUT}$ through the output terminal Tout. The impedance conversion circuit 1121 is a current conversion circuit having low input impedance and high output impedance.

Circuits equivalent to the signal transmission circuit 1100 and the signal transmission circuit 1101 are disclosed in Japanese Unexamined Patent Application, First Publication No. 2004-23135.

The signal transmission circuit 100 will be described. It is now assumed that the resistance value R of the feedback resistor R12 is 1 [kΩ]. It is also assumed that the maximum value $V_{IN\_MAX}$ of the voltage value $V_{IN}$ of the input signal VIN is 2.0 [V] and the minimum value $V_{IN\_MIN}$ of the voltage value $V_{IN}$ of the input signal VIN is 1.0 [V]. It is also assumed that the maximum value $V_{IN\_MAX}$ of the current value IN input to the impedance conversion circuit 1120 is 2.0 [mA] and the minimum value $I_{IN\_MIN}$ of the current value $I_{IN}$ is 1.0 [mA]. When the voltage value $V_{IN}$ of the input signal VIN is the maximum value $V_{IN\_MAX}$, the current value IN is the maximum value $I_{IN\_MAX}$. When the voltage value $V_{IN}$ of the input signal VIN is the minimum value $V_{IN\_MIN}$, the current value $I_{IN}$ is the minimum value $I_{IN\_MIN}$. The current value $I_{OUT}$ output from the impedance conversion circuit 1120 is expressed by expression (21).

$$I_{OUT} = -I_{IN} \quad (21)$$

The voltage value $V_{OUT}$ of the output signal VOUT is expressed by expression (22). In expression (22), $V_{REF}$ is the voltage value of the reference voltage. In expression (22), R is the resistance value of the feedback resistor R12.

$$V_{OUT} = V_{REF} - R \times I_{OUT} \quad (22)$$

When the voltage value $V_{REF}$ of the reference voltage is 1.0 [V], the maximum value $V_{OUT\_MAX}$ of the voltage value $V_{OUT}$ of the output signal VOUT is 3.0 [V] and the minimum value $V_{OUT\_MIN}$ of the voltage value $V_{OUT}$ of the output signal VOUT is 2.0 [V] according to the expressions (21) and (22). When the voltage value $V_{IN}$ of the input signal VIN is the maximum value $V_{IN\_MAX}$, the voltage value $V_{OUT}$ is the maximum value $V_{OUT\_MAX}$. When the voltage value $V_{IN}$ of the input signal VIN is the minimum value $V_{IN\_MIN}$, the voltage value $V_{OUT}$ is the minimum value V $V_{OUT\_MIN}$.

As described above, the voltage value $V_{OUT}$ of the output signal VOUT is 2.0 [V] to 3.0 [V]. Since the voltage value $V_{REF}$ of the reference voltage is 1.0 [V], the current-voltage conversion circuit 1130 needs linear output characteristics in a range of 1.0 [V] to 3.0 [V]. Thus, the current-voltage conversion circuit 1130 needs linear output characteristics even in a range of 1.0 [V] to 2.0 [V] which is not within the range of the voltage value of the output signal VOUT. This is because an offset current (1.0 [mA]) due to an offset voltage (1.0 [V]) corresponding to the minimum value $V_{IN\_MIN}$ of the voltage value $V_{IN}$ of the input signal VIN is output from the impedance conversion circuit 1120. A subsequent circuit needs linear input characteristics in the same range as the above range. For example, the subsequent circuit is an AD conversion circuit.

In the signal transmission circuit 1101, the same phenomena as described above occur depending on a constant current ($I_2$) flowing through the current source CS11 and a constant current ($I_1$) flowing through the current source CS12.

SUMMARY OF THE INVENTION

According to a first aspect of the present invention, a signal transmission circuit includes an impedance conversion circuit and a current-voltage conversion circuit. A first current is input to the impedance conversion circuit. The impedance conversion circuit is configured to output a second current according to the first current. The current-voltage conversion circuit is configured to convert the second current output from the impedance conversion circuit into a voltage. The impedance conversion circuit includes a first current source and a current output circuit. The first current source is configured to generate a reference current. The current output circuit is configured to output the second current according to a difference between the first current and the reference current or a sum of the first current and the reference current.

According to a second aspect of the present invention, in the first aspect, the signal transmission circuit may further include a switch disposed between the impedance conversion circuit and the current-voltage conversion circuit and configured to switch between on and off states of an electrical connection between the impedance conversion circuit and the current-voltage conversion circuit. The impedance conversion circuit may be configured to convert the first current input to the impedance conversion circuit into the reference current when the switch is off. The first current source may be configured to hold the reference current when the switch is off. The impedance conversion circuit may be configured to output the second current when the switch is on.

According to a third aspect of the present invention, in the second aspect, the impedance conversion circuit may further include a first transistor and a second transistor. The first transistor and the second transistor may constitute a current mirror. The first current source and the second transistor may be connected in series between a first power supply and a second power supply. The first current may be input to the first transistor. The second transistor may be connected to the switch.

According to a fourth aspect of the present invention, in the second aspect, the current output circuit may further include a transistor and a second current source. The first current source, the transistor, and the second current source may be connected in series between a first power supply and a second power supply. The transistor may have a first terminal, a second terminal, and a control terminal. The first terminal may be connected to the switch and the control terminal may be connected to a third power supply. The first current source may be connected to the first terminal. The second current source may be connected to the second terminal. The first current may be input to the terminal different from the terminal, to the second terminal.

According to a fifth aspect of the present invention, an endoscope system includes an endoscope and the signal transmission circuit. The endoscope includes an imaging device and a transmission buffer. The imaging device is configured to output an imaging signal. The transmission buffer is disposed inside or outside the imaging device and is configured to output the first current based on the imaging signal. The signal transmission circuit is connected to the transmission buffer.

DETAILED DESCRIPTION OF THE INVENTION

Embodiments of the present invention will be described with reference to the drawings.

First Embodiment

Figure 1:
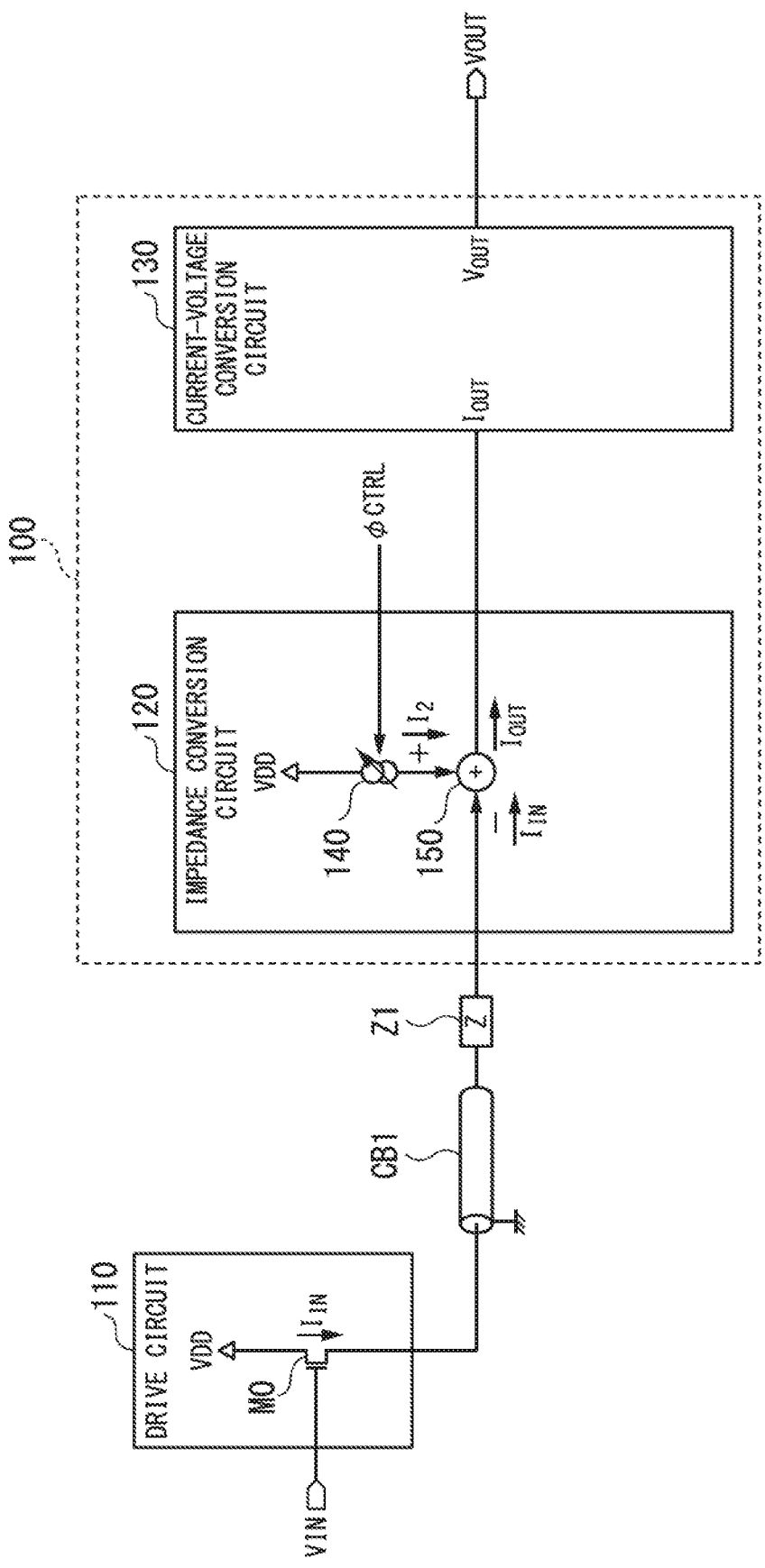
FIG. 1 is a circuit diagram showing a configuration of a signal transmission circuit according to a first embodiment of the present invention.

FIG. 1 shows a configuration of a signal transmission circuit 100 according to a first embodiment of the present invention. As shown in FIG. 1, the signal transmission circuit 100 has an impedance conversion circuit 120 and a current-voltage conversion circuit 130. The impedance conversion circuit 120 and the current-voltage conversion circuit 130 constitute a signal processing circuit. A drive circuit 110 is disposed at the input side of the signal transmission circuit 100.

The drive circuit 110 has the transistor M0. The transistor M0 is an NMOS transistor. The transistor M0 has a source terminal, a drain terminal, and a gate terminal. A drain terminal of the transistor M0 is connected to a power supply VDD. A source terminal of the transistor M0 is connected to a transmission cable CB1. An input signal VIN is input to a gate terminal of the transistor M0. The drive circuit 110 converts the input signal VIN into a first current according to transconductance gm of the transistor M0. The current value of the first current is $I_{IN}$. The first current generated by the drive circuit 110 is input to the impedance conversion circuit 120 via the transmission cable CB1 and a matching element Z1 for impedance matching.

In FIG. 1, the matching element Z1 is disposed between the transmission cable CB1 and the impedance conversion circuit 120. The matching element Z1 may be disposed between the drive circuit 110 and the transmission cable CB1. The matching elements Z1 may also be arranged between the drive circuit 110 and the transmission cable CB1 and between the transmission cable CB1 and the impedance conversion circuit 120.

A first current generated by the drive circuit 110 is input to the impedance conversion circuit 120. The impedance conversion circuit 120 outputs a second current according to the first current. The impedance conversion circuit 120 is a current conversion circuit having low input impedance and high output impedance. The impedance conversion circuit 120 has a current source 140 and a current output circuit 150.

The current source 140 is a constant current source. The current source 140 generates a reference current. A current value of a current output from the current source 140 is controlled by a control signal φCTRL. The current output circuit 150 outputs a second current according to a difference between the first current and the reference current.

The current value of the first current input to the impedance conversion circuit 120 is $I_{IN}$ and the current value of the reference current is $I_2$. The current value $I_{OUT}$ of the second current output from the impedance conversion circuit 120 is expressed by expression (1).

$$I_{OUT}=I_2-I_{IN} \qquad (1)$$

The second current output from the impedance conversion circuit 120 is input to the current-voltage conversion circuit 130. The current-voltage conversion circuit 130 converts the second current into a voltage and outputs the voltage as the output signal VOUT.

The voltage value $V_{OUT}$ of the output signal VOUT is expressed by expression (2). In expression (2), $V_{REF}$ is the voltage value of the reference voltage of the current-voltage conversion circuit 130. In expression (2), R is the resistance value of the internal resistance of the current-voltage conversion circuit 130.

$$V_{OUT}=V_{REF}-R \times I_{OUT} \qquad (2)$$

It is now assumed that the resistance value R of the internal resistance of the current-voltage conversion circuit 130 is 1 [kΩ]. It is also assumed that the maximum value $V_{IN\_MAX}$ of the voltage value $V_{IN}$ of the input signal VIN is 2.0 [V] and the minimum value $V_{IN\_MIN}$ of the voltage value $V_{IN}$ of the input signal VIN is 1.0 [V]. It is also assumed that the maximum value $I_{IN\_MAX}$ of the current value $I_{IN}$ input to the impedance conversion circuit 120 is 2.0 [mA] and the minimum value $V_{IN\_MIN}$ of the current value $I_{IN}$ is 1.0 [mA]. When the voltage value $V_{IN}$ of the input signal VIN is the maximum value $V_{IN\_MAX}$, the current value $I_{IN}$ is the maximum value $I_{IN\_MAX}$. When the voltage value $V_{IN}$ of the input signal VIN is the minimum value $V_{IN\_MIN}$, the current value $I_{IN}$ is the minimum value $I_{IN\_MIN}$.

The current value $I_2$ of the reference current is controlled such that it becomes equal to the current value input to the impedance conversion circuit 120 when an input signal VIN at a reference level is input to the signal transmission circuit 100. The voltage value $V_{IN}$ of the input signal VIN at the reference level is the same as the maximum value $V_{IN\_MAX}$. At this time, a current value input to the impedance conversion circuit 120 is the maximum value $I_{IN\_MAX}$. Therefore, a current value $I_{OUT}$ output from the impedance conversion circuit 120 is expressed by expression (3) according to the expression (1).

$$I_{OUT}=I_{IN\_MAX}-I_{IN} \qquad (3)$$

When the current value $I_{IN}$ is in a range of 1.0 [mA] to 2.0 [mA] and the current value $I_{IN\_MAX}$ is 2.0 [mA], the current value $I_{OUT}$ output from the impedance conversion circuit 120 is expressed by expression (4) according to the expression (3).

$$0 \leq I_{OUT} \leq I_{IN\_MAX}-I_{IN\_MIN} \qquad (4)$$

As shown in expression (4), when an input signal VIN having the maximum value $V_{IN\_MAX}$ is input to the signal transmission circuit 100, a current value $I_{OUT}$ output from the impedance conversion circuit 120 is zero. Therefore, the current value $I_{OUT}$ output from the impedance conversion circuit 120 includes no offset current.

When the voltage value $V_{REF}$ of the reference voltage is 1.0 [V], the maximum value $V_{OUT\_MAX}$ of the voltage value $V_{OUT}$ of the output signal VOUT is 1.0 [V] and the minimum value $V_{OUT\_MIN}$ of the voltage value $V_{OUT}$ of the output signal VOUT is 0 [V] according to the expressions (2) and (4). That is, the current-voltage conversion circuit 130 needs linear output characteristics in a range of 0 [V] to 1.0 [V]. Therefore, the voltage range in which the current-voltage conversion circuit 130 needs linear output characteristics is reduced compared to the related art. As a result, it becomes easy to design the current-voltage conversion circuit 130.

The current output circuit 150 may output a second current according to the sum of the first current and the reference current. The reference current may include a constant current component. The second current may be a current obtained by removing the constant current component from the sum of the first current and the reference current.

As described above, the signal transmission circuit 100 has the impedance conversion circuit 120 and the current-voltage conversion circuit 130. The first current is input to the impedance conversion circuit 120. The impedance conversion circuit 120 outputs a second current according to the first current. The current-voltage conversion circuit 130 converts the second current output from the impedance conversion circuit 120 into a voltage. The impedance conversion circuit 120 has the current source 140 (first current source) and the current output circuit 150. The current source 140 generates a reference current. The current output circuit 150 outputs a second current according to the difference between the first current and the reference current or the sum of the first current and the reference current.

The signal transmission circuit of each embodiment of the present invention need not have components corresponding to at least one of the drive circuit 110, the transmission cable CB1, and the matching element Z1.

In the first embodiment, the current output circuit 150 outputs a second current according to the difference between the first current and the reference current or the sum of the first current and the reference current. Therefore, the signal transmission circuit 100 can reduce an offset current based on an offset voltage of the input signal.

Modification of First Embodiment

Figure 2:
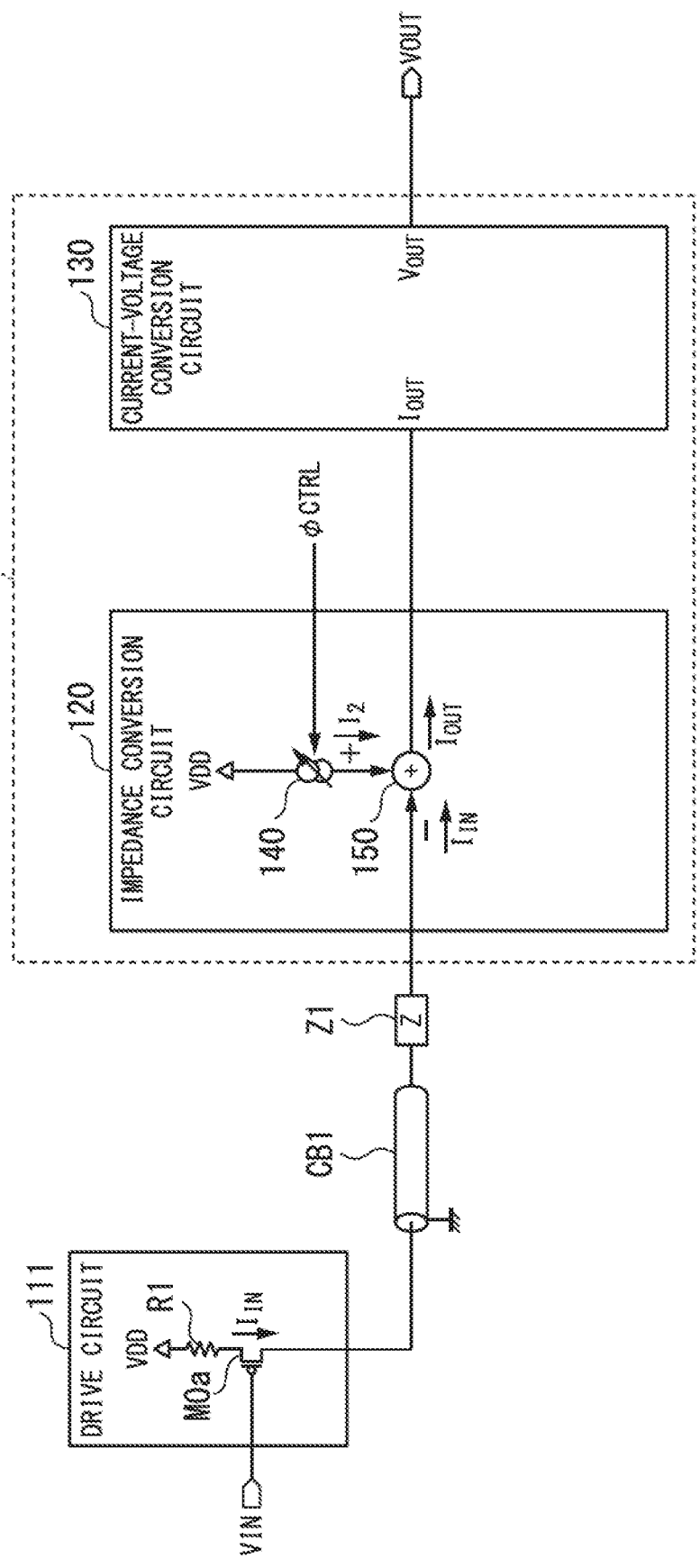
FIG. 2 is a circuit diagram showing a configuration of a signal transmission circuit according to a modification of the first embodiment of the present invention.

FIG. 2 shows a configuration of a signal transmission circuit 101 according to a modification of the first embodiment. As shown in FIG. 2, the signal transmission circuit 101 has an impedance conversion circuit 120 and a current-voltage conversion circuit 130. The signal transmission circuit 101 is identical to the signal transmission circuit 100 shown in FIG. 1. Differences of the configuration shown in FIG. 2 from the configuration shown in FIG. 1 will be described.

A drive circuit 111 is disposed at the input side of the signal transmission circuit 101. The drive circuit 111 has a transistor M0a and a resistor R1. The resistor R1 has a first terminal and a second terminal. The first terminal of the resistor R1 is connected to a power supply VDD. The transistor M0a is a PMOS transistor. The transistor M0a has a source terminal, a drain terminal, and a gate terminal. The source terminal of the transistor M0a is connected to the second terminal of the resistor R1. The drain terminal of the transistor M0a is connected to a transmission cable CB1. An input signal VIN is input to the gate terminal of the transistor M0a. The drive circuit 11 outputs a current according to the voltage of the input signal VIN and the resistance value of the resistor R1.

Other than the above points, the configuration shown in FIG. 2 is similar to that shown in FIG. 1.

The drive circuit 111 outputs a current according to the resistance value of the resistor R1. Therefore, it is easy to design the current value output by the drive circuit 111.

Second Embodiment

Figure 3:
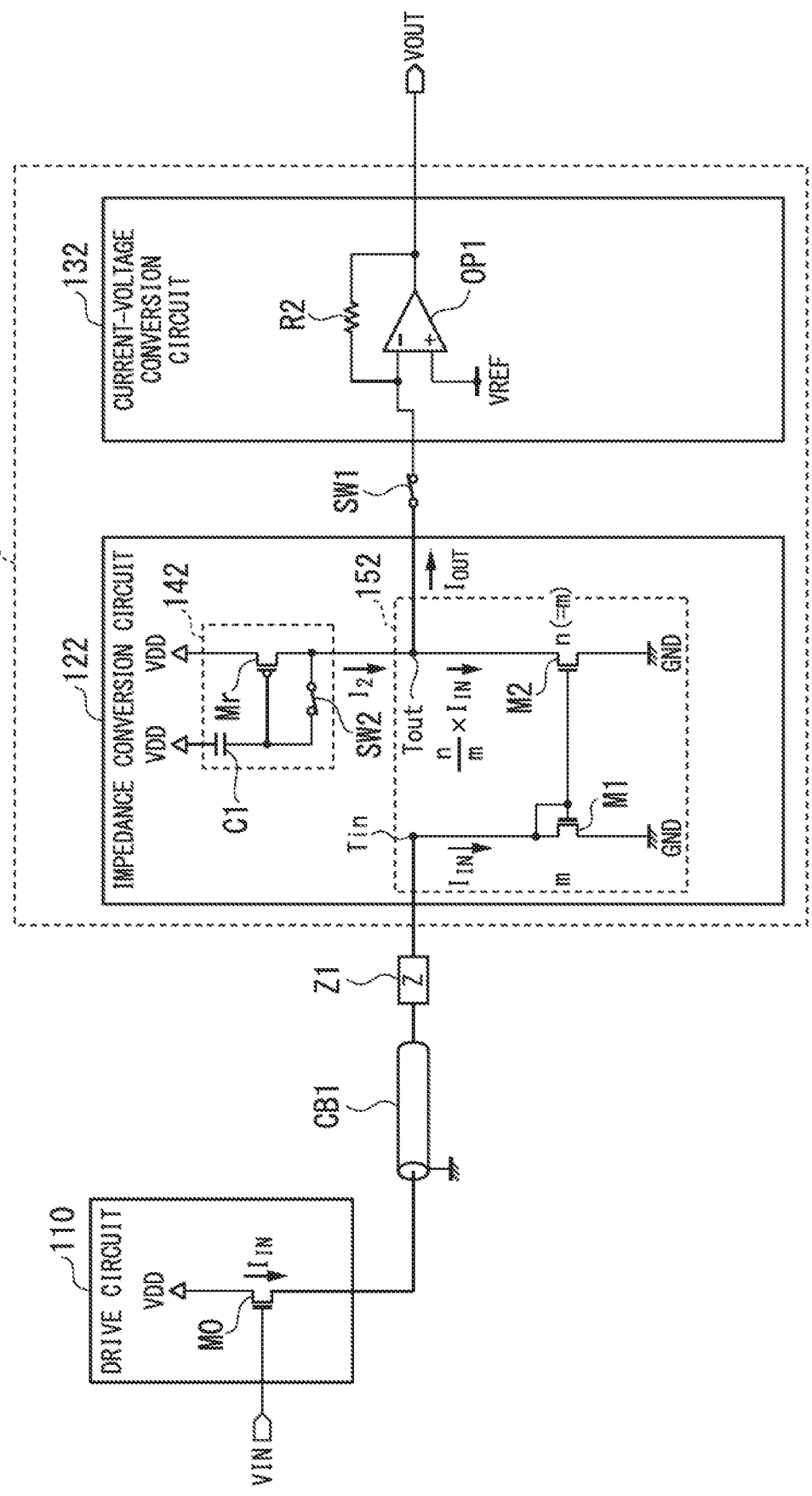
FIG. 3 is a circuit diagram showing a configuration of a signal transmission circuit according to a second embodiment of the present invention.

FIG. 3 shows a configuration of a signal transmission circuit 102 according to a second embodiment of the present invention. As shown in FIG. 3, the signal transmission circuit 102 has an impedance conversion circuit 122, a current-voltage conversion circuit 132, and a switch SW1. The impedance conversion circuit 122 and the current-voltage conversion circuit 132 constitute a signal processing circuit. Differences of the configuration shown in FIG. 3 from the configuration shown in FIG. 1 will be described.

The impedance conversion circuit 122 has a current source 142 and a current output circuit 152. The current source 142 has a transistor Mr, a switch SW2, and a capacitive element C1. For example, the transistor Mr is a PMOS transistor. The transistor Mr has a source terminal, a drain terminal, and a gate terminal.

The source terminal of the transistor Mr is connected to a power supply VDD. The drain terminal of the transistor Mr is connected to an output terminal Tout. The gate terminal of the transistor Mr is connected to the capacitive element C1. A current according to the voltage of the capacitive element C1 flows between the source and drain terminals of the transistor Mr.

The switch SW2 has a first terminal and a second terminal. The first terminal of the switch SW2 is connected to the gate terminal of the transistor Mr. The second terminal of the switch SW2 is connected to the drain terminal of the transistor Mr.

The switch SW2 is an element which can switch between on and off states. When the switch SW2 is on, the first terminal of the capacitive element C1 is electrically connected to the output terminal Tout.

The capacitive element C1 has a first terminal and a second terminal. The first terminal of the capacitive element C1 is connected to the gate terminal of the transistor Mr and the first terminal of the switch SW2. The second terminal of the capacitive element C1 is connected to the power supply VDD.

The switch SW2 and the capacitive element C1 constitute a sample hold circuit. The switch SW2 samples the voltage of the output terminal Tout. The capacitive element C1 holds the voltage sampled by the switch SW2. That is, the capacitive element C1 is a sampling capacitance.

The current source 142 is a constant current source. The current value of the current output from the current source 142 is $I_2$.

The current output circuit 152 has a transistor M1 and a transistor M2 which constitute a current mirror. The transistors M1 and M2 are NMOS transistors. The transistor M and the transistor M2 have a source terminal, a drain terminal, and a gate terminal. The drain terminal of the transistor M1 is connected to the input terminal Tin. The source terminal of the transistor M1 is connected to ground GND. The gate terminal of the transistor M1 is connected to the drain terminal of the transistor M1. The drain terminal of the transistor M2 is connected to the output terminal Tout. The source terminal of the transistor M2 is connected to the ground GND. The gate terminal of the transistor M2 is connected to the gate terminal of the transistor M1. The transistor M2 is connected to the switch SW1 via the output terminal Tout. The current source 142 and the transistor M2 are connected in series between the power supply VDD and the ground GND.

A first current generated by the drive circuit 110 is input to the input terminal Tin. The first current is input to the transistor M1 via the input terminal Tin. The first current flows between the drain and source terminals of the transistor M1. A current according to a mirror ratio of the transistors M and M2 flows between the drain and source terminals of the transistor M2. It is now assumed that the W/L ratios of the transistors M and M2 are the same. When the coefficient of the transistor M is m and the coefficient of the transistor M2 is n, the current value of the current flowing through the transistor M2 is $(n/m) \times I_{IN}$. When the coefficients of the transistors M1 and M2 are the same, the currents flowing through the transistors M1 and M2 are the same. The impedance conversion circuit 122 outputs a current whose current value is $I_{OUT}$ through the output terminal Tout. The impedance conversion circuit 122 is a current conversion circuit having low input impedance and high output impedance.

The switch SW1 is disposed between the impedance conversion circuit 122 and the current-voltage conversion circuit 132. The switch SW1 has a first terminal and a second terminal. The first terminal of the switch SW1 is connected to the impedance conversion circuit 122. The second terminal of the switch SW1 is connected to the current-voltage conversion circuit 132.

The switch SW1 switches between on and off states of the electrical connection between the impedance conversion circuit 122 and the current-voltage conversion circuit 132. When the switch SW1 is on, the impedance conversion circuit 122 and the current-voltage conversion circuit 132 are electrically connected to each other. When the switch SW1 is off, the impedance conversion circuit 122 and the current-voltage conversion circuit 132 are electrically insulated from each other.

The current-voltage conversion circuit 132 has a feedback resistor R2 and an operational amplifier OP1. The feedback resistor R2 has a first terminal and a second terminal. The operational amplifier OP1 has a non-inverting input terminal, an inverting input terminal, and an output terminal. The first terminal of the feedback resistor R2 is connected to the inverting input terminal of the operational amplifier OP1. The second terminal of the feedback resistor R2 is connected to the output terminal of the operational amplifier OP1. The inverting input terminal of the operational amplifier OP1 is connected to the second terminal of the switch SW1. The non-inverting input terminal of the operational amplifier OP1 is connected to a power supply that outputs a reference voltage VREF.

The current output from the impedance conversion circuit 122 is input to the current-voltage conversion circuit 132. The current-voltage conversion circuit 132 converts the current into a voltage and outputs the voltage as an output signal VOUT.

Other than the above points, the configuration shown in FIG. 3 is similar to that shown in FIG. 1.

The operation of the signal transmission circuit 102 will be described. For ease of explanation, it is now assumed that the mirror ratio of the transistors M1 and M2 is 1. As the input signal VIN each of a signal at a reference level and a signal at a signal level is input to the signal transmission circuit 102. When the voltage value $V_{IN}$ of the input signal VIN at the signal level is the maximum value $V_{IN\_MAX}$, the current value $I_{IN}$ is the maximum value $I_{IN\_MAX}$. When the voltage value $V_{IN}$ of the input signal VIN at the signal level is the minimum value $V_{IN\_MIN}$, the current value $I_{IN}$ is the minimum value $I_{IN\_MIN}$. The maximum value $V_{IN\_MAX}$ of the voltage value $V_{IN}$ of the input signal VIN and the minimum value $V_{IN\_MIN}$ of the voltage value $V_{IN}$ of the input signal VIN are known. The voltage value $V_{IN}$ of the input signal VIN at the reference level is the same as the maximum value $V_{IN\_MAX}$ of the voltage value $V_{IN}$ of the input signal VIN.

In a first period, the switch SW1 is controlled to be off and the switch SW2 is controlled to be on. Thereby, the impedance conversion circuit 122 and the current-voltage conversion circuit 132 are electrically insulated from each other. The input signal VIN at the reference level is input to the signal transmission circuit 102.

When the input signal VIN at the reference level is input to the signal transmission circuit 102, the current value $I_{IN}$ of the first current input to the impedance conversion circuit 122 is $I_{IN\_MAX}$. The first current is input to the transistor M1. The transistor M2 outputs a reference current having the same current value as the first current. Since the switch SW1 is off, the same current as the current flowing through the transistor M2 flows through the transistor Mr. That is, the reference current flows through the transistor Mr. A voltage required for the reference current to flow through the transistor Mr is sampled in the capacitive element C1 by the switch SW2. The capacitive element C1 holds the sampled voltage.

In a second period subsequent to the first period, the switch SW1 is controlled to be on and the switch SW2 is controlled to be off. As a result, the impedance conversion circuit 122 and the current-voltage conversion circuit 132 are electrically connected to each other. The current value $I_2$ of the current flowing through the transistor Mr is also fixed at $I_{IN\_MAX}$.

Thereafter, an input signal VIN at the signal level is input to the signal transmission circuit 102. The current output circuit 152 outputs a second current according to the difference between the first current and the reference current. The current value $I_{OUT}$ of the second current is expressed by expression (5).

$$I_{OUT} = I_{IN\_MAX} - I_{IN} \tag{5}$$

The voltage value $V_{OUT}$ of the output signal VOUT is expressed by expression (2) shown in the first embodiment.

It is now assumed that the resistance value R of the internal resistance of the current-voltage conversion circuit 132 is 1 [kΩ]. It is also assumed that the maximum value $V_{IN\_MAX}$ of the voltage value $V_{IN}$ of the input signal VIN is 2.0 [V] and the minimum value $V_{IN\_MIN}$ of the voltage value $V_{IN}$ of the input signal VIN is 1.0 [V]. It is also assumed that the maximum value $I_{IN\_MAX}$ of the current value $I_{IN}$ input to the impedance conversion circuit 122 is 2.0 [mA] and the minimum value $I_{IN\_MIN}$ of the current value $I_{IN}$ is 1.0 [mA].

When the current value IN is in a range of 1.0 [mA] to 2.0 [mA] and the current value $I_{IN\_MAX}$ is 2.0 [mA], the current value $I_{OUT}$ output from the impedance conversion circuit 122 is expressed by expression (6) according to the expression (5).

$$0 \leq I_{OUT} \leq I_{IN\_MAX} - I_{IN\_MIN} \tag{6}$$

As shown in the expression (6), when an input signal VIN having the maximum value $V_{IN\_MAX}$ is input to the signal transmission circuit 102, a current value $I_{OUT}$ output from the impedance conversion circuit 122 is zero. Therefore, the current value $I_{OUT}$ output from the impedance conversion circuit 122 includes no offset current.

According to the expression (6), the current value $I_{OUT}$ of the second current is in a range of 0 [mA] to 1.0 [mA]. When the voltage value $V_{REF}$ of the reference voltage is 1.0 [V], the maximum value $V_{OUT\_MAX}$ of the voltage value $V_{OUT}$ of the output signal VOUT is 1.0 [V] and the minimum value $V_{OUT\_MIN}$ of the voltage value $V_{OUT}$ of the output signal VOUT is 0 [V] according to the expression (2). That is, the current-voltage conversion circuit 132 needs linear output characteristics in a range of 0 [V] to 1.0 [V]. Therefore, the voltage range in which the current-voltage conversion circuit 132 needs linear output characteristics is reduced compared to the related art. As a result, it becomes easy to design the current-voltage conversion circuit 132.

The conductivity type of each transistor used in the signal transmission circuit 102 may be opposite to the above conductivity type. Although a metal oxide semiconductor (MOS) transistor is used in the signal transmission circuit 102, a bipolar transistor may be used.

As described above, the signal transmission circuit 102 has the switch SW1. The switch SW1 is disposed between the impedance conversion circuit 122 and the current-voltage conversion circuit 132 and switches between on and off states of the electrical connection between the impedance conversion circuit 122 and the current-voltage conversion circuit 132. The impedance conversion circuit 122 converts the first current input to the impedance conversion circuit 122 into the reference current when the switch SW1 is off. The current source 142 (first current source) holds the reference current when the switch SW1 is off. The impedance conversion circuit 122 outputs the second current when the switch SW1 is on.

The impedance conversion circuit 122 has the transistor M1 (first transistor) and the transistor M2 (second transistor). The transistor M1 and the transistor M2 constitute a current mirror. The current source 142 and the transistor M2 are connected in series between the first power supply (power supply VDD) and the second power supply (ground GND). The first current is input to the transistor M1. The transistor M2 is connected to the switch SW1.

In the second embodiment, the signal transmission circuit 102 can reduce an offset current based on an offset voltage of the input signal, similar to the first embodiment.

First Modification

Figure 4:
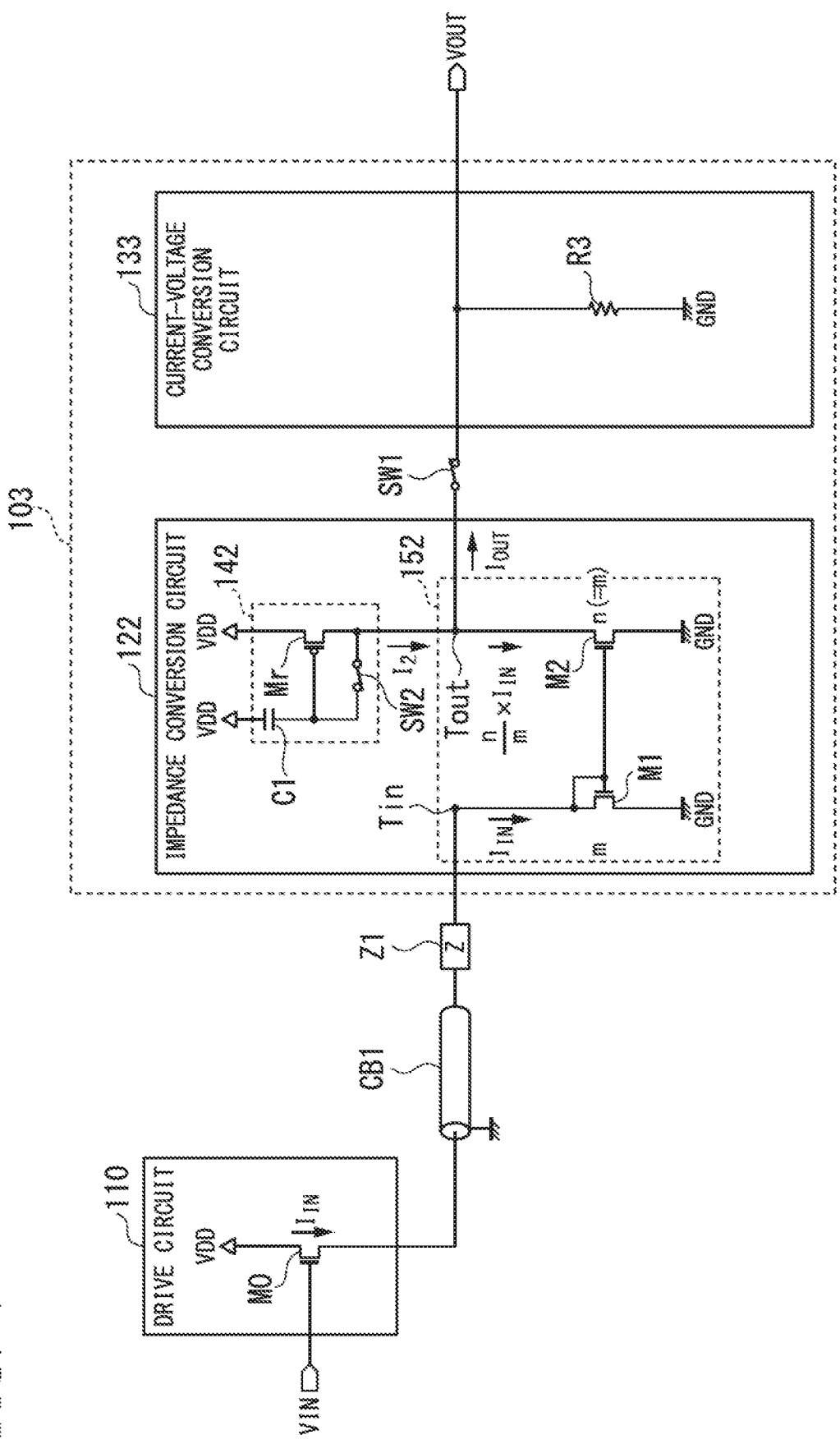
FIG. 4 is a circuit diagram showing a configuration of a signal transmission circuit according to a first modification of the second embodiment of the present invention.

FIG. 4 shows a configuration of a signal transmission circuit 103 according to a first modification of the second embodiment. As shown in FIG. 4, the signal transmission circuit 103 has an impedance conversion circuit 122, a current-voltage conversion circuit 133, and a switch SW1. The impedance conversion circuit 122 and the current-voltage conversion circuit 133 constitute a signal processing circuit. Differences of the configuration shown in FIG. 4 from the configuration shown in FIG. 3 will be described.

In the signal transmission circuit 103, the current-voltage conversion circuit 132 shown in FIG. 3 is replaced with the current-voltage conversion circuit 133. The current-voltage conversion circuit 133 has a resistor R3. The resistor R3 has a first terminal and a second terminal. The first terminal of the resistor R3 is connected to the second terminal of the switch SW1. The second terminal of the resistor R3 is connected to the ground GND.

Other than the above points, the configuration shown in FIG. 4 is similar to that shown in FIG. 3.

Second Modification

Figure 5:
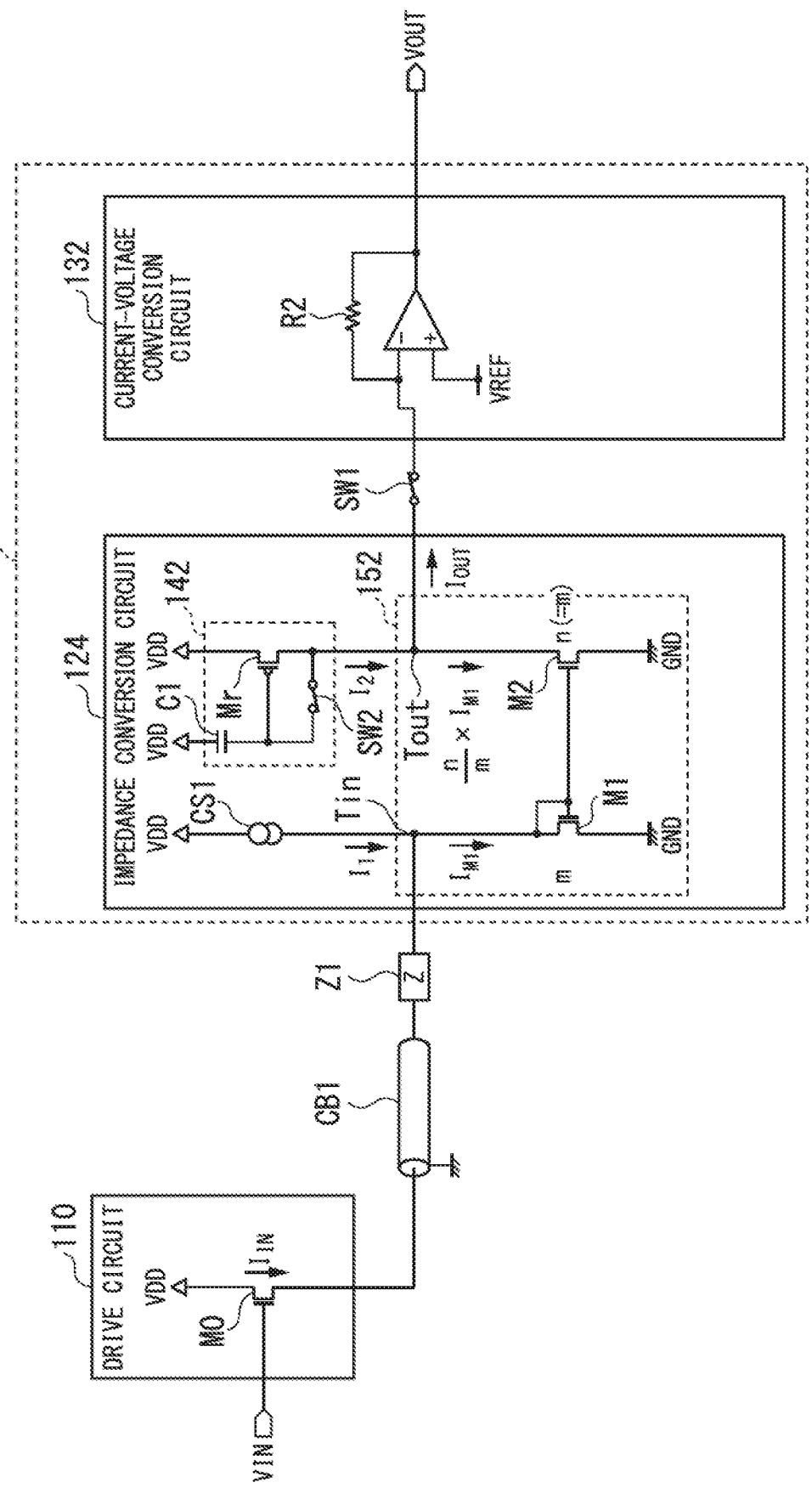
FIG. 5 is a circuit diagram showing a configuration of a signal transmission circuit according to a second modification of the second embodiment of the present invention.

FIG. 5 shows a configuration of a signal transmission circuit 104 according to a second modification of the second embodiment. As shown in FIG. 5, the signal transmission circuit 104 has an impedance conversion circuit 124, a current-voltage conversion circuit 132, and a switch SW1. The impedance conversion circuit 124 and the current-voltage conversion circuit 132 constitute a signal processing circuit. Differences of the configuration shown in FIG. 5 from the configuration shown in FIG. 3 will be described.

In the signal transmission circuit 104, the impedance conversion circuit 122 shown in FIG. 3 is replaced with the impedance conversion circuit 124. The impedance conversion circuit 124 has a current source 142, a current output circuit 152, and a current source CS1.

The current source CS1 has a first terminal and a second terminal. The first terminal of the current source CS1 is connected to a power supply VDD. The second terminal of the current source CS1 is connected to an input terminal Tin. The current source CS1 is a constant current source. The current value of the current output from the current source CS1 is $I_1$.

Other than the above points, the configuration shown in FIG. 5 is similar to that shown in FIG. 3.

The sum ($I_{M1}$) of a current ($I_{IN}$) input to the impedance conversion circuit 124 and a current ($I_1$) output by the current source CS1 flows through the transistor M1. The current flowing through the transistor M1 can be changed according to the current output from the current source CS1. This increases the degree of freedom in designing the current output circuit 152.

Third Embodiment

Figure 6:
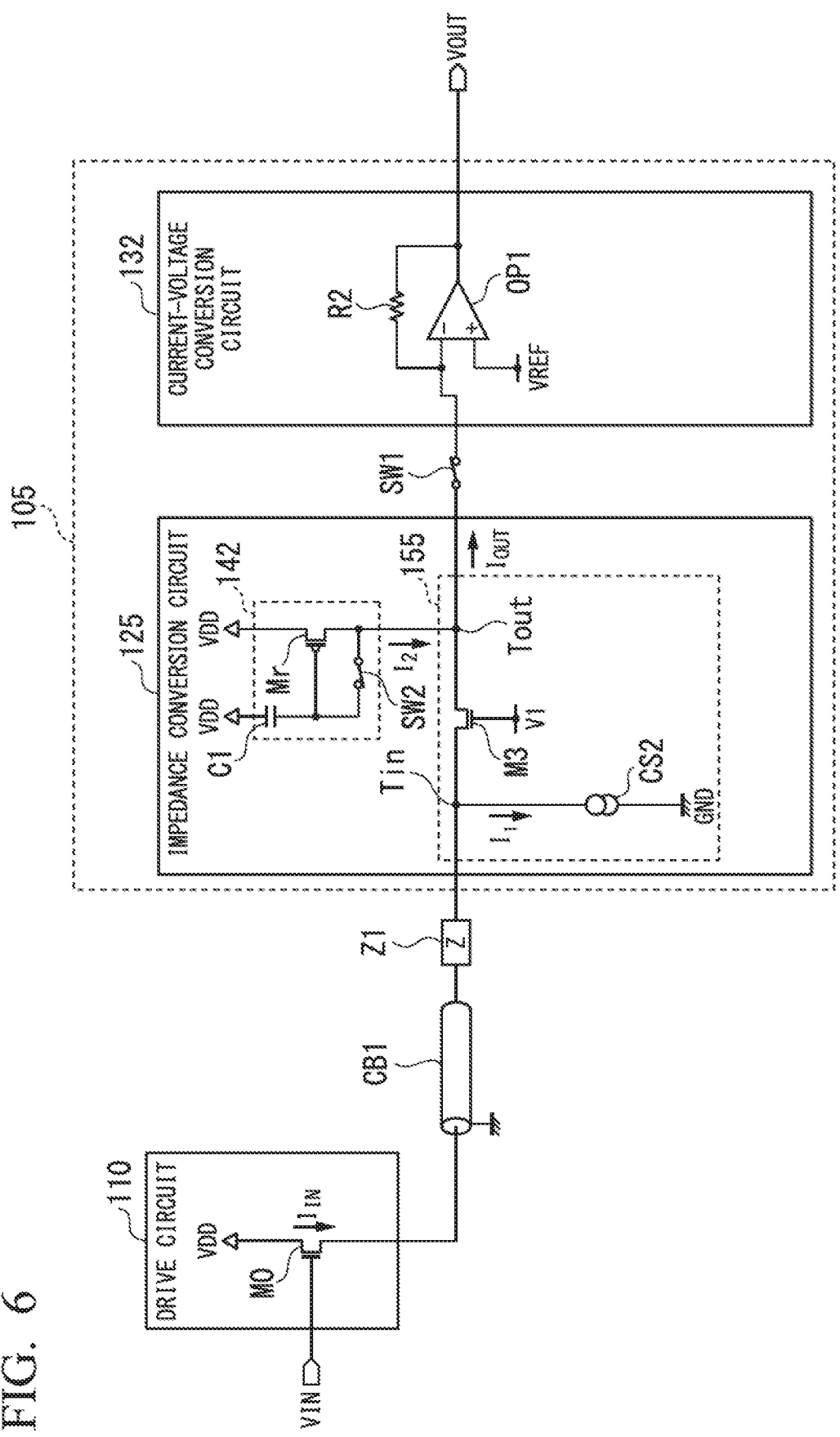
FIG. 6 is a circuit diagram showing a configuration of a signal transmission circuit according to a third embodiment of the present invention.

FIG. 6 shows a configuration of a signal transmission circuit 105 according to a third embodiment of the present invention. As shown in FIG. 6, the signal transmission circuit 105 has an impedance conversion circuit 125, a current-voltage conversion circuit 132, and a switch SW1. The impedance conversion circuit 125 and the current-voltage conversion circuit 132 constitute a signal processing circuit. Differences of the configuration shown in FIG. 6 from the configuration shown in FIG. 3 will be described.

In the signal transmission circuit 105, the impedance conversion circuit 122 shown in FIG. 3 is replaced with the impedance conversion circuit 125. The impedance conversion circuit 125 has a current source 142 and a current output circuit 155. The current output circuit 155 has a transistor M3 and a current source CS2.

The transistor M3 is an NMOS transistor. The transistor M3 is a gate-grounded transistor. The transistor M3 has a source terminal, a drain terminal, and a gate terminal. The source terminal of the transistor M3 is connected to an input terminal Tin. The drain terminal of the transistor M3 is connected to an output terminal Tout. Accordingly, the drain terminal of the transistor M3 is connected to the switch SW1 and the current source 142 via the output terminal Tout. The gate terminal of the transistor M3 is connected to a power supply V1. The power supply V1 may be identical to the power supply VDD.

The current source CS2 has a first terminal and a second terminal. The first terminal of the current source CS2 is connected to the input terminal Tin. The second terminal of the current source CS2 is connected to ground GND. The current source CS2 is a constant current source. The current value of the current output from the current source CS2 is $I_1$. The current source 142, the transistor M3, and the current source CS2 are connected in series between the power supply VDD and the ground GND.

A first current generated by the drive circuit 110 is input to the input terminal Tin. The first current is input to the source terminal of the transistor M3 via the input terminal Tin. The sum of a current value $I_{IN}$ input to the impedance conversion circuit 125 and a current value $I_2$ flowing through the current source 142 is equal to the sum of a current value $I_1$ flowing through the current source CS2 and a current value $I_{OUT}$ output from the output terminal Tout. That is, expression (7) is satisfied.

$$I_{IN}+I_2=I_1+I_{OUT} \quad (7)$$

The impedance conversion circuit 125 outputs a current whose current value is $I_{OUT}$ through the output terminal Tout. The impedance conversion circuit 125 is a current conversion circuit having low input impedance and high output impedance.

Other than the above points, the configuration shown in FIG. 6 is similar to that shown in FIG. 3.

The operation of the signal transmission circuit 105 will be described. As the input signal VIN, each of a signal at a reference level and a signal at a signal level is input to the signal transmission circuit 105. When the voltage value $V_{IN}$ of the input signal VIN at the signal level is the maximum value $V_{IN\_MAX}$, the current value $I_{IN}$ is the maximum value $I_{IN\_MAX}$. When the voltage value $V_{IN}$ of the input signal VIN at the signal level is the minimum value $V_{IN\_MIN}$, the current value $I_{IN}$ is the minimum value $I_{IN\_MIN}$. The maximum value $V_{IN\_MAX}$ of the voltage value $V_{IN}$ of the input signal VIN and the minimum value $V_{IN\_MIN}$ of the voltage value $V_{IN}$ of the input signal VIN are known. The voltage value $V_{IN}$ of the input signal VIN at the reference level is the same as the maximum value $V_{IN\_MAX}$ of the voltage value $V_{IN}$ of the input signal VIN.

In a first period, the switch SW1 is controlled such that it is turned off and the switch SW2 is controlled such that it is turned on. As a result, the impedance conversion circuit 125 and the current-voltage conversion circuit 132 are electrically insulated from each other. The input signal VIN at the reference level is input to the signal transmission circuit 105.

When the input signal VIN at the reference level is input to the signal transmission circuit 105, the current value $I_{IN}$ of the first current input to the impedance conversion circuit 125 is $I_{IN\_MAX}$. Since the switch SW1 is off, $I_{OUT}$ is zero in expression (7). Therefore, expression (8) is satisfied.

$$I_{IN\_MAX} + I_2 = I_1 \quad (8)$$

A current having a current value $I_2$ satisfying the expression (8) flows through the transistor Mr. That is, the reference current flows through the transistor Mr. A voltage required for the reference current to flow through the transistor Mr is sampled in the capacitive element C1 by the switch SW2. The capacitive element C1 holds the sampled voltage. The current value $I_2$ of the reference current is expressed by expression (9). The reference current includes the current (constant current component) output from the current source CS2.

$$I_2 = I_1 - I_{IN\_MAX} \quad (9)$$

In a second period subsequent to the first period, the switch SW1 is controlled such that it is turned on and the switch SW2 is controlled such that it is turned off. As a result, the impedance conversion circuit 125 and the current-voltage conversion circuit 132 are electrically connected to each other. The current value $I_2$ of the current flowing through the transistor Mr is also fixed at the value indicated by the expression (9).

Thereafter, an input signal VIN at the signal level is input to the signal transmission circuit 105. The current output circuit 155 outputs a second current. The current value $I_{OUT}$ of the second current is expressed by expression (10) according to the expressions (7) and (9). That is, the current output circuit 155 outputs a second current according to the sum of the first current and the reference current. The second current is a current obtained by subtracting the constant current component of the current source CS2 from the sum of the first current and the reference current.

$$I_{OUT} = I_{IN} + I_2 - I_1 = I_{IN} - I_{IN\_MAX} \quad (10)$$

The voltage value $V_{OUT}$ of the output signal VOUT is expressed by expression (2) shown in the first embodiment.

It is now assumed that the resistance value R of the internal resistance of the current-voltage conversion circuit 132 is 1 [kΩ]. It is also assumed that the maximum value $V_{IN\_MAX}$ of the voltage value $V_{IN}$ of the input signal VIN is 2.0 [V] and the minimum value $V_{IN\_MIN}$ of the voltage value $V_{IN}$ of the input signal VIN is 1.0 [V]. It is also assumed that the maximum value $I_{IN\_MAX}$ of the current value IN input to the impedance conversion circuit 125 is 2.0 [mA] and the minimum value $I_{IN\_MIN}$ of the current value IN is 1.0 [mA].

When the current value $I_{IN}$ is in a range of 1.0 [mA] to 2.0 [mA] and the current value $I_{IN\_MIN}$ is 2.0 [mA], the current value $I_{OUT}$ output from the impedance conversion circuit 125 is expressed by expression (11) according to the expression (10).

$$I_{IN\_MIN} - I_{IN\_MAX} \le I_{OUT} \le 0 \quad (11)$$

As shown in the expression (11), when an input signal VIN having the maximum value $V_{IN\_MAX}$ is input to the signal transmission circuit 105, a current value $I_{OUT}$ output from the impedance conversion circuit 125 is zero. Therefore, the current value $I_{OUT}$ output from the impedance conversion circuit 125 includes no offset current.

According to the expression (11), the current value $I_{OUT}$ of the second current is in a range of −1.0 [mA] to 0 [mA]. When the voltage value $V_{REF}$ of the reference voltage is 1.0 [V], the maximum value $V_{OUT\_MAX}$ of the voltage value $V_{OUT}$ of the output signal VOUT is 2.0 [V] according to the expression (2) and the minimum value $V_{OUT\_MIN}$ of the voltage value $V_{OUT}$ of the output signal VOUT is 1.0 [V]. That is, the current-voltage conversion circuit 132 needs linear output characteristics in a range of 1.0 [V] to 2.0 [V]. Therefore, the voltage range in which the current-voltage conversion circuit 132 needs linear output characteristics is reduced compared to the related art. As a result, it becomes easy to design the current-voltage conversion circuit 132.

The conductivity type of each transistor used in the signal transmission circuit 105 may be opposite to the above conductivity type. Although a metal oxide semiconductor (MOS) transistor is used in the signal transmission circuit 105, a bipolar transistor may also be used.

The current-voltage conversion circuit 133 may be used instead of the current-voltage conversion circuit 132. The impedance conversion circuit 125 may have a current source CS1.

As described above, the current output circuit 155 has the transistor M3 and the current source CS2 (second current source). The current source 142, the transistor M3, and the current source CS2 are connected in series between the first power supply (power supply VDD) and the second power supply (ground GND). The transistor M3 has a first terminal (drain terminal), a second terminal (source terminal), and a control terminal (gate terminal). The first terminal is connected to the switch SW1 and the control terminal is connected to the power supply V1 (third power supply). The current source 142 is connected to the first terminal. The current source CS2 is connected to the second terminal. A first current is input to the second terminal.

In the third embodiment, the signal transmission circuit 105 can reduce an offset current based on an offset voltage of the input signal, similar to the first embodiment.

Fourth Embodiment

Figure 7:
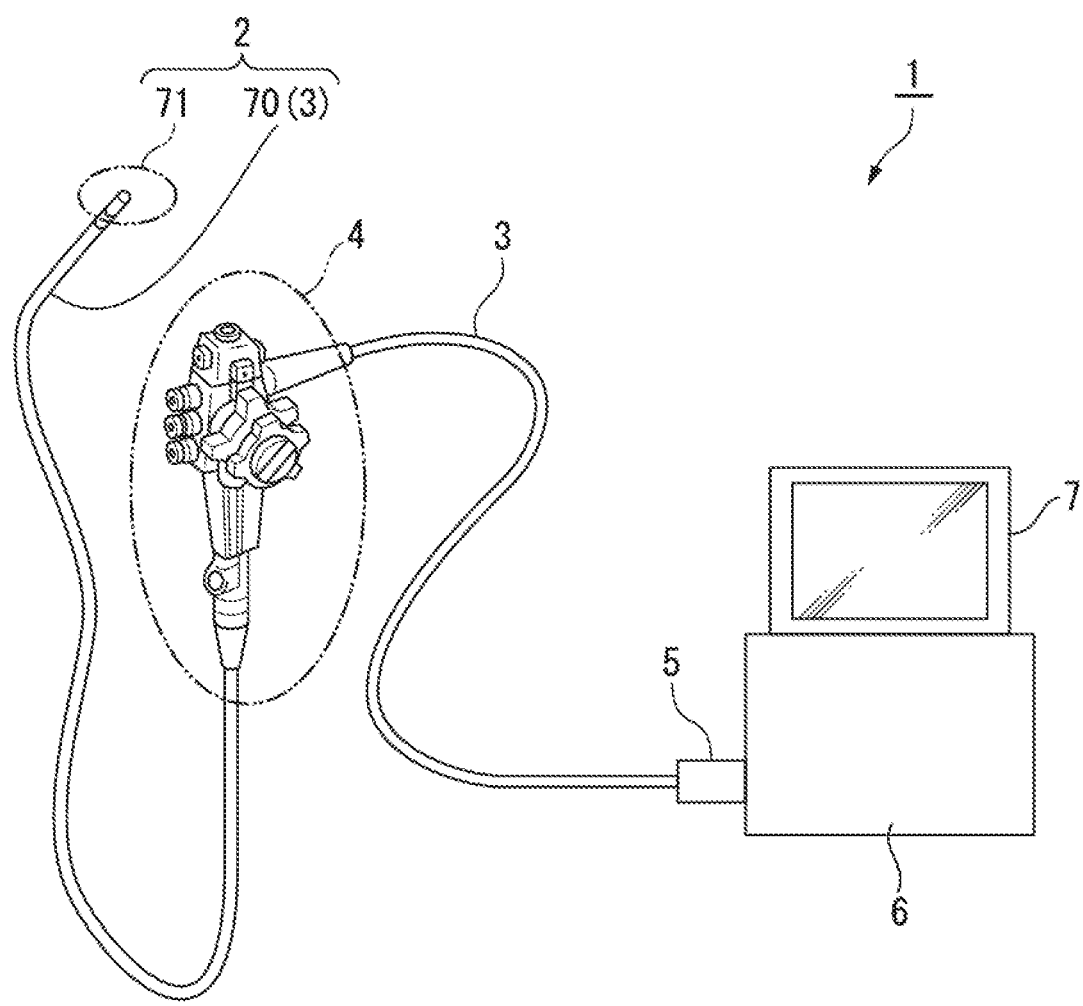
FIG. 7 is a schematic diagram showing a configuration of an endoscope system according to a fourth embodiment of the present invention.

FIG. 7 shows a configuration of an endoscope system 1 according to a fourth embodiment of the present invention.

As shown in FIG. 7, the endoscope system 1 includes an endoscope 2, a transmission cable 3, a manipulation unit 4, a connector unit 5, a processor 6, and a display device 7.

Figure 8:
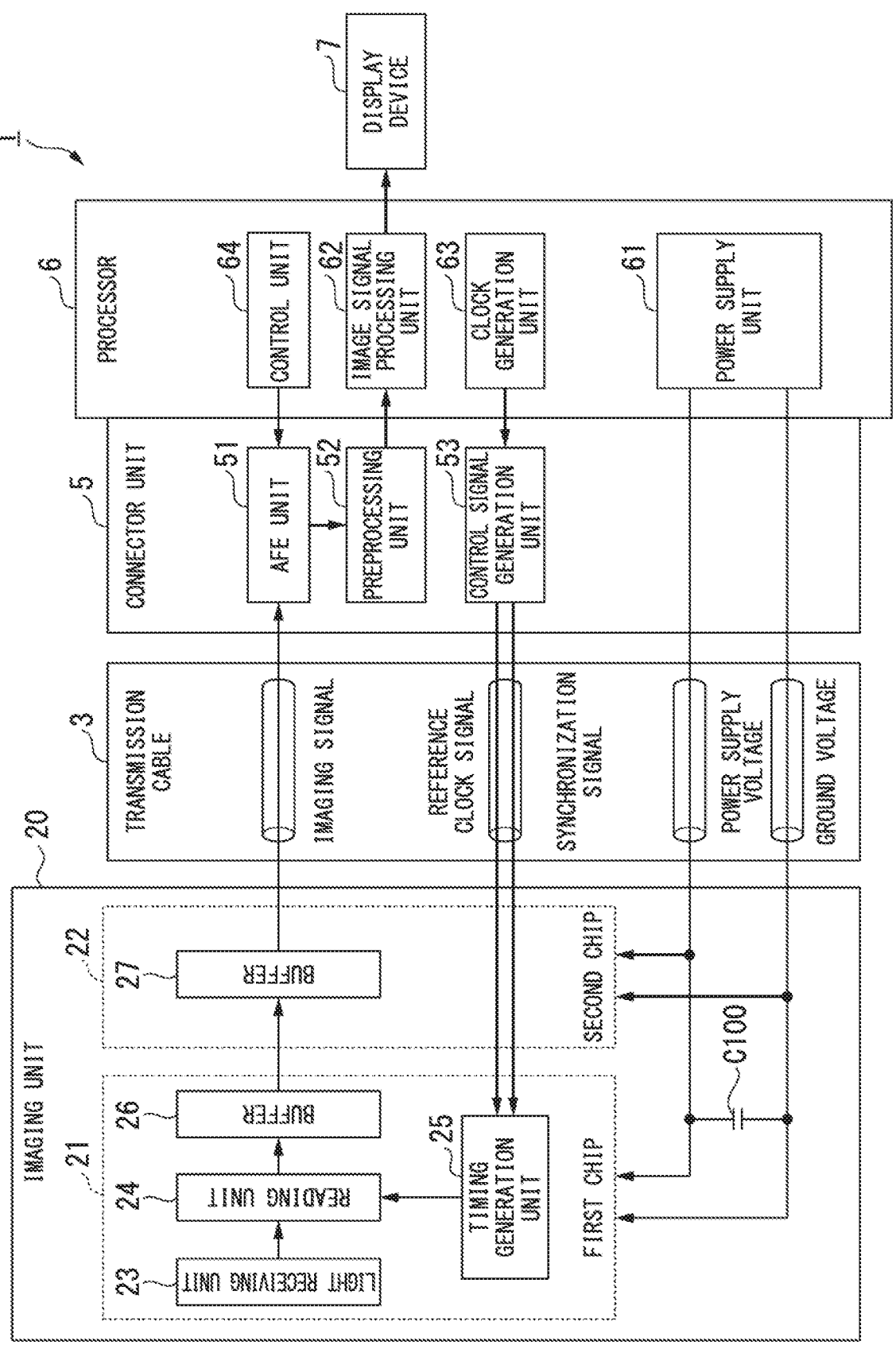
FIG. 8 is a block diagram showing a configuration of the endoscope system according to the fourth embodiment of the present invention.
Figure 9:
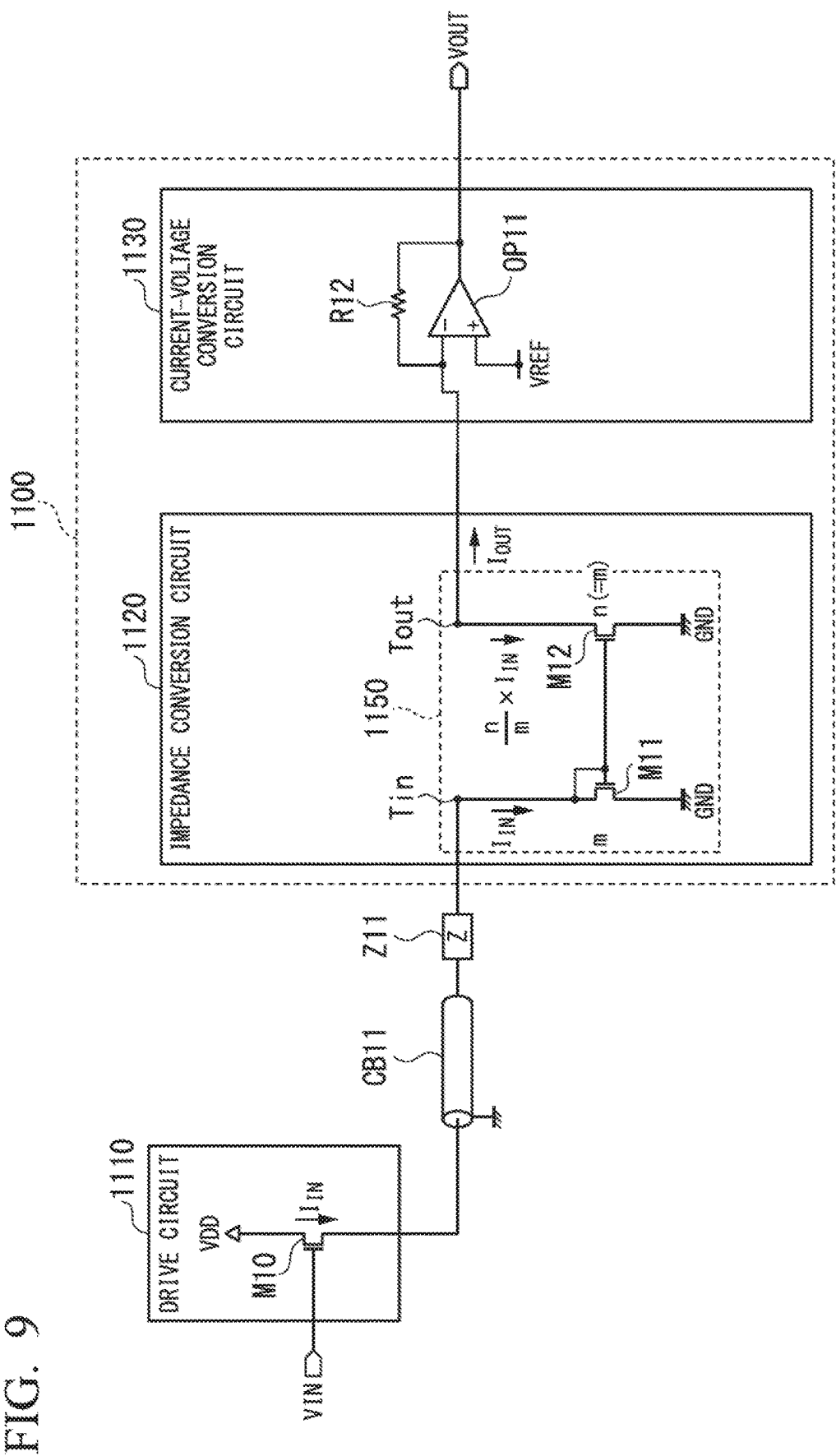
FIG. 9 is a circuit diagram showing a configuration of a signal transmission circuit according to a related art.
Figure 10:
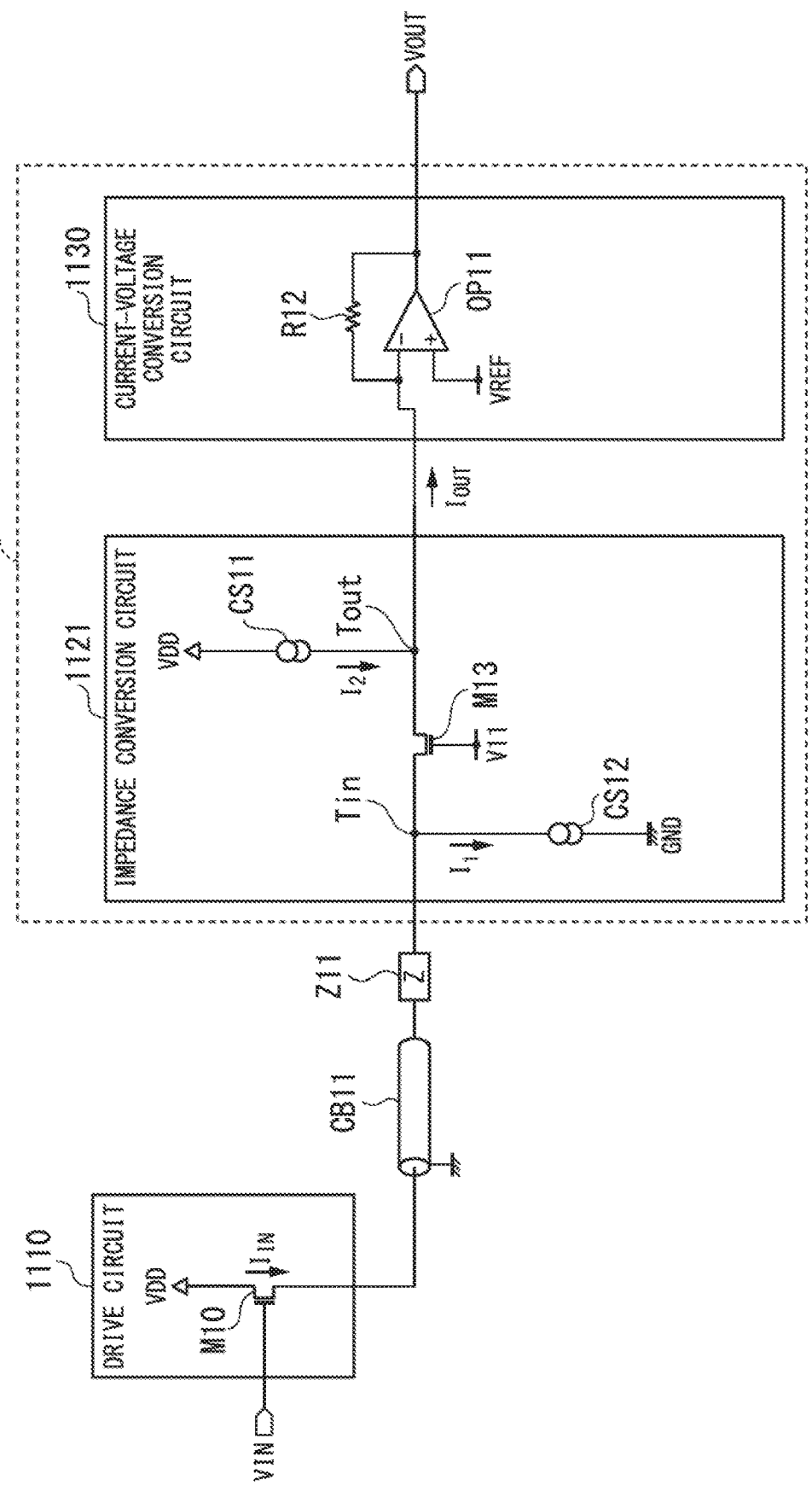
FIG. 10 is a circuit diagram showing a configuration of a signal transmission circuit according to a related art.

The endoscope 2 has an insertion portion 70 for insertion into a subject. The insertion portion 70 is a part of the transmission cable 3. The insertion portion 70 is inserted into the subject. The endoscope 2 generates an imaging signal (image data) by capturing an internal image of the subject. The endoscope 2 outputs the generated imaging signal to the processor 6. An imaging unit 20 shown in FIG. 8 is disposed at a distal end 71 of the insertion portion 70. The manipulation unit 4 is connected to an end portion of the insertion portion 70 opposite to the distal end 71. The manipulation unit 4 receives various manipulations on the endoscope 2.

The transmission cable 3 connects the imaging unit 20 of the endoscope 2 and the connector unit 5. The imaging signal generated by the imaging unit 20 is output to the connector unit 5 via the transmission cable 3.

The connector unit 5 is connected to the endoscope 2 and the processor 6. The connector unit 5 performs predetermined signal processing on the imaging signal output from the endoscope 2. The connector unit 5 also A/D) converts an analog imaging signal into a digital imaging signal. The connector unit 5 outputs the digital imaging signal to the processor 6.

The processor 6 performs predetermined image processing on the imaging signal output from the connector unit 5 and generates an image signal. The processor 6 also totally controls the entire endoscope system 1.

The display device 7 displays an image corresponding to the image signal processed by the processor 6. The display device 7 also displays various types of information on the endoscope system 1.

The endoscope system 1 has a light source device for generating illumination light with which a subject is irradiated. The light source device is omitted in FIG. 7.

FIG. 8 shows an internal configuration of the endoscope system 1. As shown in FIG. 8, the endoscope system 1 includes the imaging unit 20, the transmission cable 3, the connector unit 5, and the processor 6.

The imaging unit 20 has a first chip 21 and a second chip 22. The first chip 21 includes a light receiving unit 23, a reading unit 24, a timing generation unit 25, and a buffer 26. The imaging unit 20 functions as an imaging device. The imaging unit 20 outputs an imaging signal.

The light receiving unit 23 has a plurality of pixels and generates an imaging signal based on incident light. The reading unit 24 reads the imaging signal generated by the light receiving unit 23. The reading unit 24 also generates a reference signal. The timing generation unit 25 generates a timing signal on the basis of a reference clock signal and a synchronization signal output from the connector unit 5. The timing signal generated by the timing generation unit 25 is output to the reading unit 24. The reading unit 24 reads the imaging signal in accordance with the timing signal. The buffer 26 temporarily holds the imaging signal and the reference signal read from the light receiving unit 23. The first chip 21 outputs the imaging signal through the buffer 26.

The second chip 22 has a buffer 27. The buffer 27 outputs the imaging signal output from the first chip 21 to the connector unit 5 via the transmission cable 3. The buffer 27 includes a drive circuit 110 or a drive circuit 111. The imaging signal is input to the drive circuit 110 or the drive circuit 111 as an input signal VIN. The combination of circuits mounted on the first chip 21 and the second chip 22 can be appropriately changed according to design. In the endoscope system 1 shown in FIG. 8, the buffer 27 is disposed inside the imaging unit 20. The buffer 27 may also be disposed inside the endoscope 2 and outside the imaging unit 20.

A power supply voltage and a ground voltage generated by the processor 6 are transmitted to the imaging unit 20 through the transmission cable 3. In the imaging unit 20, a capacitor C100 for stabilizing the power supply is disposed between a signal line transmitting the power supply voltage and a signal line transmitting the ground voltage.

The connector unit 5 has an analog front end unit 51 (hereinafter referred to as an AFE unit 51), a preprocessing unit 52, and a control signal generation unit 53. The connector unit 5 electrically connects the endoscope 2 (the imaging unit 20) and the processor 6. The connector unit 5 and the imaging unit 20 are connected by the transmission cable 3. The transmission cable 3 corresponds to the transmission cable CB1. The connector unit 5 and the processor 6 are connected by a coil cable.

The AFE unit 51 (an imaging signal processing circuit) calculates the difference between the reference signal and the imaging signal. The AFE unit 51 also performs A/D conversion on the imaging signal based on this difference. The AFE unit 51 outputs the imaging signal, which has been converted into a digital signal by the A/D conversion, to the preprocessing unit 52. The AFE unit 51 includes one of the signal transmission circuit 100, the signal transmission circuit 101, the signal transmission circuit 102, the signal transmission circuit 103, the signal transmission circuit 104, and the signal transmission circuit 105.

The preprocessing unit 52 performs predetermined signal processing such as vertical line removal or noise removal on the digital imaging signal output from the AFE unit 51. The preprocessing unit 52 outputs the signal-processed imaging signal to the processor 6.

A reference clock signal serving as a reference for the operation of each part of the endoscope 2 is provided from the processor 6 to the control signal generation unit 53. For example, the frequency of the reference clock signal is 27 MHz. On the basis of the reference clock signal, the control signal generation unit 53 generates a synchronization signal indicating the start position of each frame. The control signal generation unit 53 outputs the reference clock signal and the synchronization signal to the timing generation unit 25 of the imaging unit 20 via the transmission cable 3. The synchronization signal generated by the control signal generation unit 53 includes a horizontal synchronization signal and a vertical synchronization signal.

The processor 6 is a control device that totally controls the entire endoscope system 1. The processor 6 has a power supply unit 61, an image signal processing unit 62, a clock generation unit 63, and a control unit 64.

The power supply unit 61 generates a power supply voltage. The power supply unit 61 outputs the power supply voltage and a ground voltage to the imaging unit 20 via the connector unit 5 and the transmission cable 3.

The image signal processing unit 62 (image signal generation circuit) performs predetermined image processing on the digital imaging signal processed by the preprocessing unit 52. The predetermined image processing is a synchronization process, a white balance (WB) adjustment process, a gain adjustment process, a gamma correction process, a digital analog (D/A) conversion process, a format conversion process, or the like. The image signal processing unit 62 converts the imaging signal into an image signal by this image processing. That is, the image signal processing unit 62 processes the imaging signal (difference signal) based on the difference calculated by the AFE unit 51 and generates an image signal based on the imaging signal. The image signal processing unit 62 outputs the generated image signal to the display device 7.

The clock generation unit 63 generates a reference clock signal which serves as a reference for the operation of each part of the endoscope system 1. The clock generation unit 63 outputs the generated reference clock signal to the control signal generation unit 53.

The control unit 64 controls the AFE unit 51 by outputting a control signal to the AFE unit 51. For example, the control unit 64 controls the current value output from the current source 140 by outputting a control signal φCTRL to the AFE unit 51. The control unit 64 controls turning on/off of the switches SW1 and SW2 by outputting a control signal to the AFE unit 51.

The display device 7 displays the image captured by the imaging unit 20 on the basis of the image signal output from the image signal processing unit 62. The display device 7 has a display panel such as a liquid crystal or organic electro luminescence (EL) display panel.

The endoscope system 1 has an endoscope 2 and a signal transmission circuit. The endoscope 2 has an imaging unit 20 (an imaging device) and a buffer 27 (a transmission buffer). The imaging unit 20 outputs an imaging signal. The buffer 27 is disposed inside or outside the imaging unit 20 and outputs a first current based on the imaging signal. The signal transmission circuit is connected to the buffer 27. The endoscope system 1 has one of the signal transmission circuit 100, the signal transmission circuit 101, the signal transmission circuit 102, the signal transmission circuit 103, the signal transmission circuit 104, and the signal transmission circuit 105.

The endoscope system of each aspect of the present invention need not have components corresponding to at least one of the transmission cable 3, the manipulation unit 4, the processor 6, and the display device 7. The endoscope system of each aspect of the present invention need not have components corresponding to at least one of the preprocessing unit 52 and the control signal generation unit 53.

The fourth embodiment has been described with respect to the endoscope system 1 having the signal transmission circuit. However, the signal transmission circuit may also be applied to devices and systems other than the endoscope system 1.

In the fourth embodiment, the endoscope system 1 can reduce an offset current based on an offset voltage of the input signal, similar to the above embodiments.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A signal transmission circuit to which a signal of each of a reference level and a signal level is input as an input signal, the signal transmission circuit comprising:
an impedance conversion circuit configured to receive a first current as an input and to output a second current according to the first current;
a current-voltage conversion circuit configured to convert the second current output from the impedance conversion circuit into a voltage; and
a switch disposed between the impedance conversion circuit and the current-voltage conversion circuit and configured to switch between on and off states of an electrical connection between the impedance conversion circuit and the current-voltage conversion circuit,
the impedance conversion circuit including:
a first current source configured to generate a reference current; and
a current output circuit configured to output the second current according to a difference between the first current and the reference current or a sum of the first current and the reference current,
wherein the switch is controlled to be off in a first period,
the impedance conversion circuit is configured to convert the first current that is based on the input signal of the reference level into the reference current in the first period,
the first current source is configured to hold the reference current converted by the impedance conversion circuit in the first period,
the switch is controlled to be on in a second period after the first period, and
the impedance conversion circuit is configured to output the second current according to the difference between or the sum of the first current that is based on the input signal of the signal level and the reference current held by the first current source in the second period.

2. The signal transmission circuit according to claim 1 wherein the impedance conversion circuit further includes a first transistor and a second transistor,
the first transistor and the second transistor constitute a current mirror,
the first current source and the second transistor are connected in series between a first power supply and a second power supply,
the first current is input to the first transistor, and
the second transistor is connected to the switch.

3. The signal transmission circuit according to claim 1, wherein the current output circuit further includes a transistor and a second current source,
the first current source, the transistor, and the second current source are connected in series between a first power supply and a second power supply,
the transistor has a first terminal, a second terminal, and a control terminal,
the first terminal is connected to the switch and the control terminal is connected to a third power supply,
the first current source is connected to the first terminal,
the second current source is connected to the second terminal, and
the first current is input to the second terminal.

4. An endoscope system, comprising:
an endoscope including:
an imaging device configured to output an imaging signal; and
a transmission buffer disposed inside or outside the imaging device and configured to output the first current based on the imaging signal; and
the signal transmission circuit according to claim 1 connected to the transmission buffer.

* * * * *